United States Patent [19]

Schulz et al.

[11] 4,137,418

[45] Jan. 30, 1979

[54] CONVERSION OF CARBONACEOUS MATERIAL

[75] Inventors: Johann G. D. Schulz, Pittsburgh; Edward T. Sabourin, Allison Park, both of Pa.

[73] Assignee: Gulf Research & Development Company, Pittsburgh, Pa.

[21] Appl. No.: 814,217

[22] Filed: Jul. 5, 1977

Related U.S. Application Data

[63] Continuation-in-part of Ser. No. 696,752, Jun. 16, 1976, Pat. No. 4,052,448.

[51] Int. Cl.$^2$ ............................................. C07C 51/16
[52] U.S. Cl. .................................................. 562/407
[58] Field of Search ........... 260/515 P, 515 H, 515 M

[56] References Cited

U.S. PATENT DOCUMENTS

| | | | |
|---|---|---|---|
| 2,555,410 | 6/1951 | Howard | 260/515 P |
| 3,153,666 | 10/1964 | Higuchi et al. | 260/515 H |
| 3,259,650 | 7/1966 | Decker et al. | 260/515 H |

OTHER PUBLICATIONS

Franke et al., Industrial & Engineering Chemistry, 44 (11), pp. 2784–2792, (1952).

Primary Examiner—Jane S. Myers

[57] ABSTRACT

A mixture of polycyclic aromatic polycarboxylic acids that is substantially soluble in acetone and substantially soluble in water and a process for preparing the mixture.

5 Claims, 1 Drawing Figure

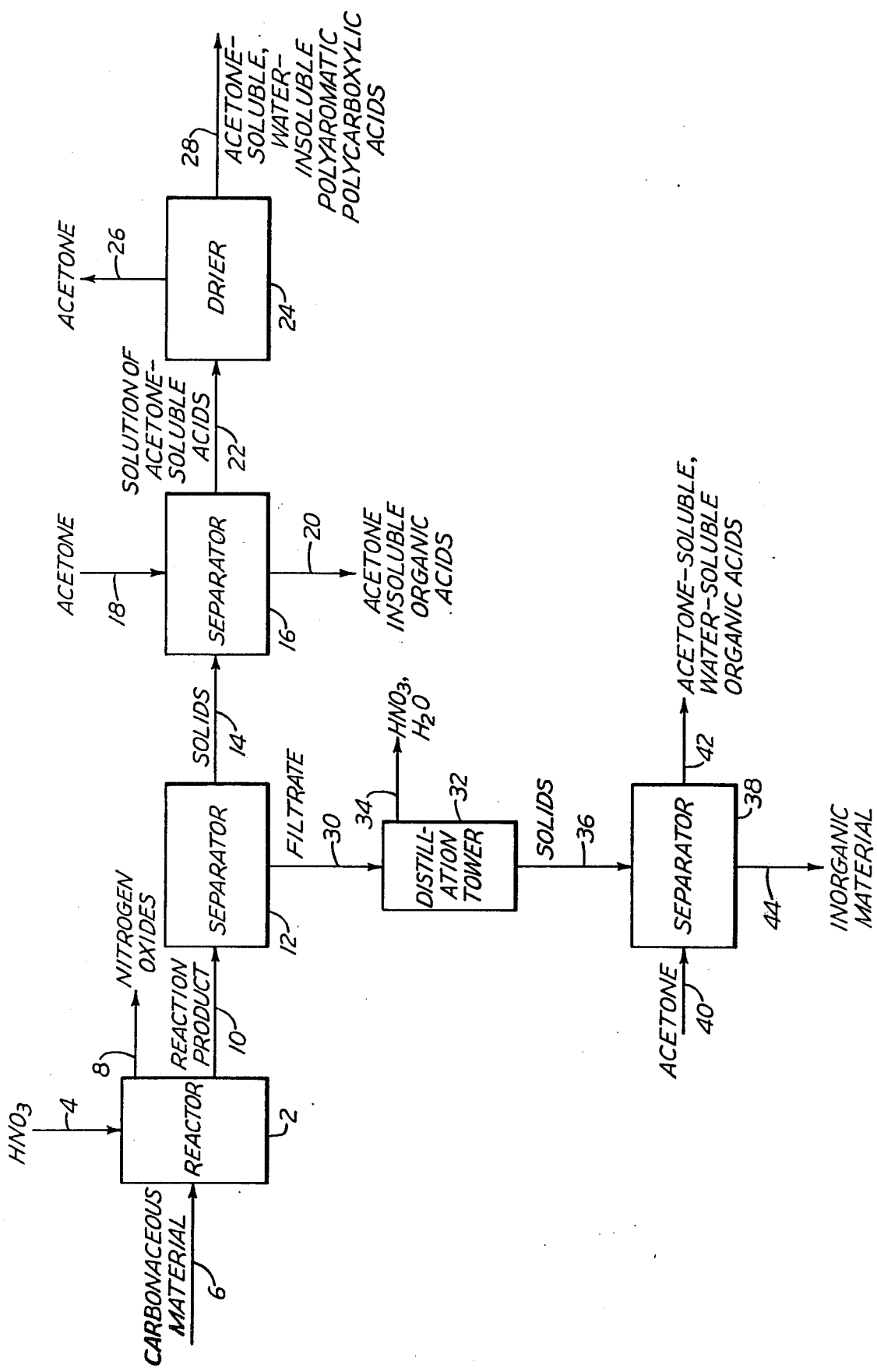

CONVERSION OF CARBONACEOUS MATERIAL

This application is a continuation-in-part application of our U.S. patent application Ser. No. 696,752, filed June 16, 1976, now U.S. Pat. No. 4,052,448, entitled Organic Acids and Process for Preparing Same.

BACKGROUND OF THE INVENTION

1. Field of the Invention

This invention relates to a mixture of polycyclic aromatic polycarboxylic acids that is substantially soluble in acetone and substantially soluble in water and a process for preparing the mixture by treating a carbonaceous material with nitric acid.

2. Description of Prior Art

Treating a carbonaceous material, such as coal, with nitric acid to obtain carboxylic acids is shown in U.S. Pat. Nos. 2,555,410 to Howard, 2,726,262 to Grosskinsky et al., 2,949,350 to Heinze et al, 2,991,189 to Rickert and 3,173,947 to Benning et al. In each of these the acids obtained are said to be water soluble. Creigton et al in U.S. Pat. No. 3,468,943 are interested in passing coal through a screw conveyor and at spaced apart intervals feeding appropriate quantities of concentrated nitric acid so that it is completely reacted with the coal before the coal arrives at the next nitric acid feed point to obtain humic acids which are said to be partially soluble in sodium hydroxide solution but substantially insoluble in water.

SUMMARY OF THE INVENTION

We have prepared novel mixtures of polycyclic aromatic polycarboxylic acids that are substantially soluble in acetone and substantially soluble in water. The individual components of said mixtures are believed to be composed of condensed and/or noncondensed benzene rings, with an average number of benzene rings in the individual molecules ranging from one to about three, but generally from one to two. On the average, the number of carboxyl groups carried by the individual molecules are believed to range from about two to about eight, generally from about two to about five and the average number of nitro groups from 0 to about 4, generally from 0 to about 2. The average molecular weight of the mixture is believed to range from about 200 to about 500, generally from about 300 to about 400, and the average neutral equivalent will range from about 50 to about 200, generally from about 70 to about 120. A typical analysis of the novel mixture is defined below in Table I in approximate amounts.

TABLE I

|  | Weight Per Cent | |
| --- | --- | --- |
|  | Broad Range | General Range |
| Carbon | 35 to 60 | 37 to 48 |
| Hydrogen | 1 to 5 | 3 to 4 |
| Nitrogen | 1 to 6 | 4 to 5 |
| Oxygen | 35 to 60 | 40 to 55 |
| Sulfur | 0.1 to 0.4 | 0.1 to 0.3 |
| Ash | 0.1 to 5 | 0.1 to 2 |

A preferred and novel procedure for obtaining the above novel mixtures is described in reference to FIG. 1. There is introduced into reactor 2 by line 4 an aqueous solution of nitric acid and by line 6 a carbonaceous material. The nitric acid can have a concentration of about five to about 90 percent, but preferably will be in the range of about 10 to about 70 percent. The carbonaceous material is preferably a solid in the form of a slurry, for example, an aqueous slurry containing the carbonaceous material in particulate form and from about 50 to about 90 weight percent of water.

The solid carbonaceous material that can be used herein can have the following composition on a moisture-free basis:

TABLE II

|  | Weight Percent | |
| --- | --- | --- |
|  | Broad Range | Preferred Range |
| Carbon | 45–95 | 60–92 |
| Hydrogen | 2.5–7 | 4–6 |
| Oxygen | 2.0–45 | 3–25 |
| Nitrogen | 0.75–2.5 | 0.75–2.5 |
| Sulfur | 0.3–10 | 0.5–6 |

The carbon and hydrogen content of the carbonaceous material will reside primarily in multi-ring aromatic compounds (condensed and/or uncondensed), heterocyclic compounds, etc. Oxygen and nitrogen are believed to be present primarily in chemical combination. Some of the sulfur is believed to be present in chemical combination with the aromatic compounds and some in chemical combination with inorganic elements associated therewith, for example, iron and calcium.

In addition to the above the solid carbonaceous material being treated herein will also contain solid, primarily inorganic, compounds which will not be converted to the desired organic mixture claimed herein, which are termed ash, and are composed chiefly of compounds of silicon, aluminum, iron and calcium, with smaller amounts of compounds of magnesium, titanium, sodium and potassium. The ash content of the carbonaceous material treated herein will amount to less than about 50 weight percent, based on the moisture-free carbonaceous material, but, in general, will amount to about 0.1 to about 30 weight percent, usually about 0.5 to about 20 weight percent.

Anthracitic, bituminous and subbituminous coal, lignitic materials, and other type of coal products referred to in ASTM D-388 are exemplary of the solid carbonaceous materials which can be treated in accordance with the process defined herein to produce the claimed organic mixture. Some of these carbonaceous materials in their raw state will contain relatively large amounts of water. These can be dried prior to use herein. The carbonaceous material, prior to use, is preferably ground in a suitable attrition machine, such as a hammermill, to a size such that at least about 50 percent of the carbonaceous material will pass through a 40-mesh (U.S. Series) sieve. As noted, the carbonaceous material is slurred in a suitable carrier, preferably water, prior to reaction with nitric acid. If desired, the carbonaceous material can be treated, prior to reaction herein, using any conventional means, to remove therefrom any materials forming a part thereof that will not be converted in reaction with nitric acid herein.

The reactant mixture in reactor 2 is stirred while being maintained at a temperature of about 15° to about 200° C., preferably about 50° to about 120° C., and a pressure of about atmospheric to about 1000 pounds per square inch gauge (about atmospheric to about 70 kilograms per square centimeter), preferably about atmospheric to about 500 pounds per square inch gauge (about atmospheric to about 35 kilograms per square centimeter) for about 0.5 to about 15 hours, preferably about 2 to about 6 hours. In order to obtain the desired mixture herein without losing appreciable amounts of carboxyl and/or nitro groups on the acids that are formed during the oxidation, and to obtain the desired acids in high yields in reactor 2, it is absolutely critical that the reaction conditions therein, namely nitric acid concentration, temperature, pressure and reaction time, be so correlated to minimize and, preferably, to avoid decarboxylation and denitrofication. Gaseous products, such as nitrogen oxides, can be removed from reaction 2 by line 8.

The reaction product is removed from reactor 2 by line 10. We have found that the reaction product is soluble in, or reactable with, sodium hydroxide. At this point it is necessary to separate the oxidized product from the water and nitric acid associated therewith. This separation must be accomplished in a manner so that the carboxyl groups are not removed from the acid product. Distillation for the removal of water will not suffice, because under the conditions required for such separation, a significant loss of carboxyl groups and nitro groups would occur. Accordingly, we have found that a mechanical separation will suffice. The reaction product in line 10 is therefore led to a separator 12, which can be, for example, a filter or a centrifuge.

The solids that are recovered in separator 12, also soluble in sodium hydroxide, are led by line 14 to a separator 16 wherein they are subjected to extraction with acetone that is introduced therein by line 18. Such separation can be carried out at a temperature of about 20° to about 60° C., preferably about 25° to about 50° C., and a pressure of about atmospheric to about 500 pounds per square inch gauge (about atmospheric to about 35 kilograms per square centimeter), preferably about atmospheric to about 100 pounds per square inch gauge (about atmospheric to about seven kilograms per square centimeter). The solid material, insoluble in acetone, is removed from separator 16 by line 20 and the acetone solution of the acid mixture by line 22. The acetone solution can then be led to drier 24 wherein acetone is separated therefrom by line 26 and an acetone-soluble, water-insoluble polyaromatic, polycarboxylic acid mixture is recovered in line 28. As before, the acid mixture in drier 24 can be treated by so correlating the conditions therein to remove acetone therefrom in such manner so as to minimize and, preferably, avoid, decarboxylation. The temperature can be in the range of about 10° to about 60° C., preferably about 20° to about 50° C., the pressure about 10 millimeters of mercury to about atmospheric, preferably about 30 millimeters of mercury to about atmospheric, for about 0.5 to about 24 hours, preferably about one to about five hours.

The filtrate obtained in separator 12 is removed therefrom by line 30. In all cases the filtrate will contain water, nitric acid and most of the inorganic material (ash) that was present in the carbonaceous charge. Additionally, it contains the desired and novel acetone-soluble, water-soluble organic acids claimed herein.

Separation of the filtrate into its component parts can be effected as follows. It can be passed to distillation tower 32 maintained at a temperature of about 50° to about 100° C., preferably about 70° to about 90° C. and a pressure of about 10 millimeters of mercury to about atmospheric, preferably about 30 millimeters of mercury to about atmospheric. Under these conditions nitric acid and water are removed from distillation tower 32 by line 34 and solids by line 36. The solids are led to separator 38 where they are subjected to extraction with acetone introduced therein by line 40. The conditions in separator 38 are similar to those used in separator 16. A mixture of the novel acetone-soluble, water-soluble organic acids claimed herein is removed from separator 38 by line 42 and substantially all of the inorganic material that was present in the carbonaceous charge by line 44.

DESCRIPTION OF PREFERRED EMBODIMENTS

Several runs were carried out in which a North Dakota Lignite analyzing as follows, on a substantially moisture-free basis, was subjected to oxidation using nitric acid as the oxidant: 65.03 weight percent carbon, 4.0 weight percent hydrogen, 27.0 weight percent oxygen, 0.92 weight percent sulfur, 0.42 weight percent nitrogen and 0.04 weight percent moisture. The ash was further analyzed and found to contain 43 weight percent oxygen, 7.8 weight percent sulfur and the remainder metals.

In each run, 100 grams of powdered lignite defined above (corresponding to 67 grams of moisture-free feed), 80 grams of water and 70 percent aqueous nitric acid were added to a reaction zone, stirred and maintained at selected temperature levels and atmospheric pressure. The reaction product was passed to a separator and the filtrate obtained was subjected to distillation to remove nitric acid and water therefrom. The remaining solids were extracted with acetone in Soxlet extractor and the extract was heated to remove acetone therefrom. The product remaining was the acetone-soluble, water-insoluble organic acids claimed herein. The results obtained are summarized below in Table III.

TABLE III

| Run No. | Total Milliliters of $HNO_3$ Total | Temperature, °C. | Reaction Time, Hours | Acetone-Soluble Water-Soluble Product, Grams | Analysis of Product, Weight Percent ||||||
|---|---|---|---|---|---|---|---|---|---|---|
| | | | | | Carbon | Hydrogen | Nitrogen | Oxygen | Sulfur | Ash |
| 1 | 75 | 50 | 5 | 1.8 | 38.87 | 3.25 | 1.80 | 54.14 | 0.20 | 1.74 |
| 2 | 150 | 75 | 5 | 22.4 | 45.23 | 3.57 | 4.30 | 44.81 | 0.19 | 1.90 |
| 3 | 225 | 75 | 5 | 24.3 | 45.97 | 3.33 | 4.50 | 44.18 | 0.17 | 1.85 |
| 4 | 225 | 110 | 5 | 21.2 | 43.54 | 3.35 | 4.60 | 46.36 | 0.15 | 2.00 |

Although we have stated above that the novel composition is acetone-soluble and water-soluble and we have shown the use of acetone as suitable in the process defined herein, this has been done merely as a characterization of the composition and to exemplify one embodiment of our process. Many polar solvents can be used in place of acetone herein. Among the polar solvents that have been used are methanol, ethanol, isopropanol, methyl ethyl ketone, tetrahydrofuran, dioxane, cyclohexanone, etc. The use of such solvents, therefore, falls within the scope of the invention claimed herein.

Since the novel mixture claimed herein has abundant functionality in both carboxyl and nitro groups, it is apparent that the mixture lends itself to many known chemical reactions, for example, esterification of the carboxyl groups, hydrogenation of the nitro groups to amines, etc. We have found that the novel mixtures defined herein can be converted to their corresponding anhydrides using conventional dehydrating conditions and that such anhydrides can be used as curing agents for epoxy resins. This is illustrated below.

RUN NO. 5

18.7 grams of EPON 828 (an epoxy resin having an ep equivalent of 0.1 and an epoxy equivalent weight of 187, manufactured by Shell Chemical Co.) and 58 grams of acetone were mixed in a 400-milliliter beaker using a magnetic stirrer. To this solution there was added with stirring 17.6 grams of the anhydride obtained from a mixture of the products from Runs Nos. 1 to 4 above having an anhydride equivalent of 0.1 and an anhydride equivalent weight of 176 until the anhydride went into solution. 0.18 gram of N,N-dimethylbenzylamine as an accelerator was then added to the resulting solution. This was done at ambient temperature and pressure.

A strip of glass cloth (EM-181-38) 6 inches wide and 39 inches long was dried in an oven at 105° C. for 10 minutes and then dipped into the above solution and air dried for five minutes. The dried glass cloth was again dipped into the solution, air dried as before and then dried for seven minutes at 80° C. The treated glass cloth was cut into six 6-inch by 6-inch panels, stacked one upon the other, placed between aluminum foil, cured in a hydraulic press for 30 minutes at 135° C. under 135 pounds per square inch gauge pressure (7.03 kilograms per square centimeter) and then cooled to ambient temperature. The calculated resin content of the laminate was 35.2 weight percent. An average flexural strength of 64,400 pounds per square inch gauge (4,527 kilograms per square centimeter) was obtained for this composition.

Obviously, many modifications and variations of the invention, as hereinabove set forth, can be made without departing from the spirit and scope thereof and, therefore, only such limitations should be imposed as are indicated in the appended claims.

We claim:

1. A process for converting a carbonaceous material selected from the group consisting of coal and lignite to a mixture of polycyclic aromatic polycarboxylic acids that is substantially soluble in acetone and soluble in water which comprises subjecting an aqueous slurry containing said carbonaceous material to reaction with aqueous nitric acid, wherein the nitric acid has a concentration of about 5 to about 90 percent and the reaction is carried out at a temperature of about 15° to about 200° C. for about 0.5 to about 15 hours, separating the solids in the resulting slurry by filtration, separating nitric acid and water from the resulting filtrate by distillation and then extracting the remainder of said filtrate with a polar solvent to obtain said mixture of polycyclic aromatic polycarboxylic acids.

2. The process of claim 1 wherein said polar solvent is acetone.

3. The process of claim 1 wherein the nitric acid has a concentration of about 10 to about 70 percent and the reaction is carried out at a temperature of about 50° to about 120° C. for about two to about six hours.

4. The process of claim 1 wherein the carbonaceous material is coal.

5. The process of claim 1 wherein the carbonaceous material is lignite.

* * * * *